United States Patent [19]

Lenoir et al.

[11] Patent Number: 4,605,305

[45] Date of Patent: Aug. 12, 1986

[54] LASER NEPHELOMETER FOR SENSING ANTIGENS AND ANTIBODIES CHARACTERIZED IN HAVING MEASURING CELL COMPRISED OF CAPILIARY TUBE WITH THE DIAMETER OF LASER BEAM

[75] Inventors: Jeannine Lenoir, Chaponost; André G. Bertoye; Renée Bertoye, both of Lyons, all of France

[73] Assignees: Centre National de la Recherche Scientifique, Paris; Institut Pasteur De Lyon Et Du Sud-Est, Lyons, both of France

[21] Appl. No.: 509,814

[22] Filed: Jun. 30, 1983

[30] Foreign Application Priority Data

Jul. 6, 1982 [FR] France .................. 82 12045

[51] Int. Cl.[4] .............. G01N 21/00; G01N 21/03; G01N 1/10; G01N 15/00
[52] U.S. Cl. .................. 356/246; 250/574; 356/244; 356/333; 356/339; 364/524; 364/525; 364/555; 364/575
[58] Field of Search ............. 356/338, 339, 246, 244; 364/525, 555, 524, 575; 250/574

[56] References Cited

U.S. PATENT DOCUMENTS

| | | | |
|---|---|---|---|
| 2,970,216 | 1/1961 | Magrath. | |
| 3,662,176 | 5/1972 | Kamentsky et al. | 356/343 X |
| 3,785,735 | 1/1974 | Friedman et al. | 356/343 X |
| 3,788,744 | 1/1974 | Friedman et al. | 356/336 X |
| 4,305,665 | 12/1981 | Achter et al. | 356/246 |
| 4,343,552 | 10/1982 | Blades | 356/246 X |
| 4,408,880 | 11/1983 | Tsuji et al. | 356/338 |
| 4,432,642 | 2/1984 | Tolles | 356/246 |

FOREIGN PATENT DOCUMENTS 0005979 12/1979 European Pat. Off..

OTHER PUBLICATIONS

Medicinal Progress Through Technology, vol. 6, No. 2, 1979, Springer-Verlag, Neidelberg, Ackerman et al., pp. 83–85, 88.

Journal of Clinical Chemistry and Clinical Biochemistry, vol. 16, No. 7, 1978, Gruyter Berlin, Baruth et al., pp. 397, 402, Behring Institut–Behring Laser Nephelometer, Dec. 1979, pp. 1–7.

Primary Examiner—John E. Kittle
Assistant Examiner—Mukund J. Shah
Attorney, Agent, or Firm—Parkhurst & Oliff

[57] ABSTRACT

A perfected laser nephelometer, characterized in that the measuring cell is comprised of a capillary tube (3) of which the inner diameter is close to the diameter of the laser beam (2).

2 Claims, 2 Drawing Figures

LASER NEPHELOMETER FOR SENSING ANTIGENS AND ANTIBODIES CHARACTERIZED IN HAVING MEASURING CELL COMPRISED OF CAPILIARY TUBE WITH THE DIAMETER OF LASER BEAM

TECHNICAL FIELD

The invention pertains to a perfected device for sensing the presence of antigens or antibodies and ultimately the dosing of the latter.

BACKGROUND

As is known, an antigen is a substance which is able to trigger the forming of antibodies and to respond specifically to them. Most of the time, they are proteins, polyosides, lipids or nucleic acids. There are several kinds of antigens:

cell antigens which characterize and classify the individual who carries them;

parasitic antigens which comprise the parasite or that are secreted by a parasite bacterial antigens which are supported by the membranes of bacteria, the corpus of bacteria, or which are secreted by bacteria virus antigens.

The introduction of an antigen into an organism which is alien to it stimulates the production of antibodies. This is an immune reaction. Antibodies belong to the class of serum globulins and they all have the properties of proteins.

Antigen and antibody molecules display several active sites. When solutions of antigens and antibodies have predetermined concentrations, their mixture produces flocculation comprised of a dense network of antigen and antibody molecules. If there is an excess of one of the molecules the reaction is not obvious.

The process can be completed by adding substance called a complement to the complex. This complement is a unit of several serum proteins other than albumen, which reacts successively in a well-established order. The complement possesses no immunological specificity, but it increases the quantity of antigen-antibody complex and it makes it visible.

Thus, the corresponding mixture of antigen and antibody solutions, in adequate proportions, produces an insoluble complex in most instances and the medium becomes opalescent. Immunological precipitation and flocculation tests are therefore based on quantifying this opalescence.

Currently, in order to sense the presence of antigens or antibodies, one of the methods uses nephelometry (a method also called turbidmetry), or the observance of the appearance of a precipitate.

In a first method, diluted amounts of antigens and antibodies are mixed, then the appearance of a cloud is observed (immunodiffusion, electrosynaeresis, precipitation test). This phenomenon only takes place after twenty-four hours or even longer, which is too long for prescribing medical doses.

In order to reduce this delay and to reduce the amounts of antigens and antibodies being used, a gel of antibodies and antigens can be used. This actually reduces the delay by half, however, this time period is still too long.

These precipitations can be observed with a laser nephelometer, or a laser device which is used to observe the turbidness of a liquid, or its particle content of a different refraction index. This technique is essentially based on the scattering light with insoluble antigen-antibody complexes which are formed in a liquid environment. The intensity of the scattered light beam is then a function of the concentration of those complexes. These nephelometers are well known, and therefore we do not have to give a detailed description of them. In summary, a laser nephelometer basically includes (for instance see Medicinal Progress Technology 6, 2 (1979) 81–90):

a luminous source which is comprised of a laser beam that is designed to transmit a coherent, monochromatic, parallel and narrow light; a photoelectric sensor which gathers light scattered under an optimal angle, 31.8 degrees for instance, that is, if need be, connected to a photomultiplier machine; and a device that provides results, either by memory input, or by direct display on a screen, or on a printer or on a tracing table.

Even though this device is well known, it still has many disadvantages which are basically related to the measuring cell which currently is comprised of a vat, the volume of which is about one $cm^3$. Such a volume displays in a medical environment serious disadvantages because usually, the amount of liquid which is available is at best one $cm^3$, and furthermore, for safety or other reasons, several measurements are conducted, especially to discover optimal precipitation conditions for the formed complex. Moreover, with this known method, the beginning and end of the reaction are detected, or the emergence of the total precipitation is detected, which requires another several hours, even with precipitation accelerating agents.

SUMMARY OF THE INVENTION

The invention alleviates those disadvantages. It pertains to a device for sensing antigens or antibodies which:

on the one hand, requires only a small amount of liquid and is therefore compatible with medical requirements, and on the other hand, makes it possible to sense more rapidly the emergence of the characteristic cloud.

This laser nephelometer is characterized in that the measuring cell is comprised of a capillary tube, with an inner diameter close to the diameter of the laser beam.

As we known, a "capillary tube" is a tube made from material that can be wetted inside when a liquid rises without suction (Jurin Law).

Thus, with the use of this capillary tube, first extremely small amounts of liquid can be used, second, the development of the reaction, instead of its beginning and end as was the case until now with the vat, and finally, adding precipitation is avoided.

More specifically amounts of corresponding antigen and antibody solutions are successively introduced by suction into the capillary tube, so that the separating surface of those two solutions can be found, when the tube is placed inside the nephelometer close to the laser beam. Once the reagents are there, the tip of the capillary is sealed, for instance with wax, then the tube is placed inside the sample holder of the nephelometer, and finally the percentage of scattered light is recorded in relation to time, which increases with the concentration of suspended particles.

Thus, as opposed to the vat method, the two antigen-antibody liquids back scatter, as in the double immunodifussion method, and flocculation begins close to the separating zone.

Furthermore, and this is one of the original characteristics of the invention, with the impact of the walls, the small dimensions of the capillary facilitates precipitation as it increases reaction kinetics, which is unobtainable with a known cell and which is an unexpected result.

Practically speaking:

as has been said already, the inner diameter of the capillary tube must be close to the diameter of the laser beam, particularity in order to recover most of the available light;

the inner diameter of the capillary tube is between 0.3 and 1.2 millimeters, and is preferably close to one millimeter. If this diameter is increased the amount of liquid used is increased, which is undesireable, and if the diameter is decreased length of the optical trajectory is decreased, which decreases the accuracy of the measurement;

The volumes of used solutions equal about one to fifteen microliters ($\mu$l);

The capillary tube can be made of glass with a regular cylindrical section, or it can be made of transparent plastic material which can be wetted (not hydrophobic).

In a first embodiment, the capillary tube can be replaced by a capillary vat with parallel sides, the laser beam being directed between the plates, parallel to them. However, this embodiment is more expensive, less accurate and less convenient to exploit.

In a second embodiment, the straight capillary tube can be replaced by a U-shaped capillary tube, in order to increase the optical trajectory. In this way, sensitivity is increased. The trajectory of the luminous beam is impinged on the horizontal branch of the U.

In another implementation, the device is equipped with automatic drawing means, which substantially increases its output.

In yet another implementation, instead of constantly recording the entire curve, periodic recordings of the specific points at regular intervals are recorded which makes it possible to treat several liquids at a time, for instance by placing the tubes on a swivel or on slides. Thus, for instance several samples can be treated in 25 minutes.

The way in which the invention can be implemented and the advantages which stem from it will be highlighted in the implementation examples that follow which are provided as non limiting illustrations, supported by the attached drawings.

DETAILED DESCRIPTION OF THE PREFFERED EMBODIMENTS

Figure 1:
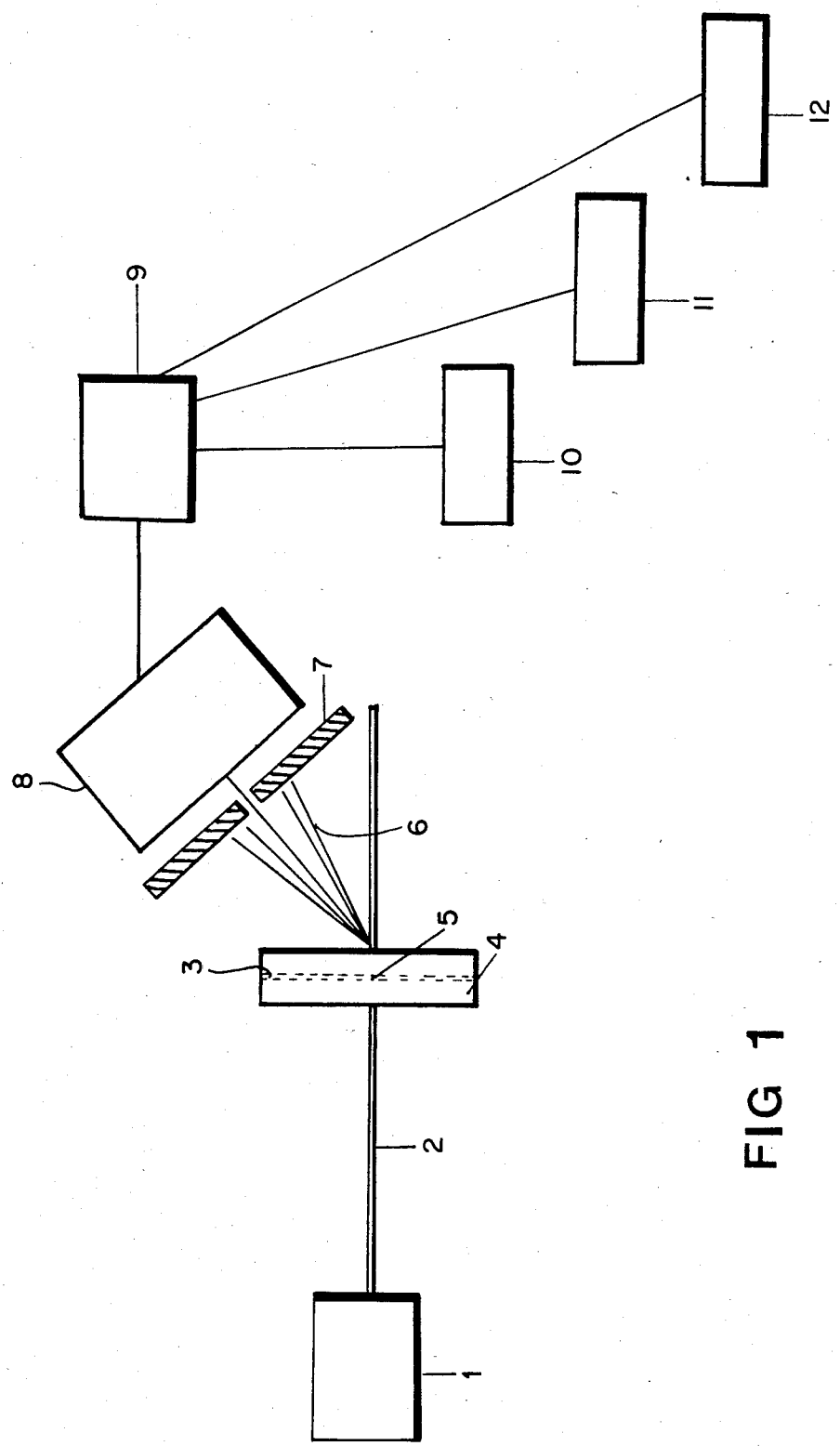
FIG. 1 depicts schematically a laser nephelometer according to the invention.
Figure 2:
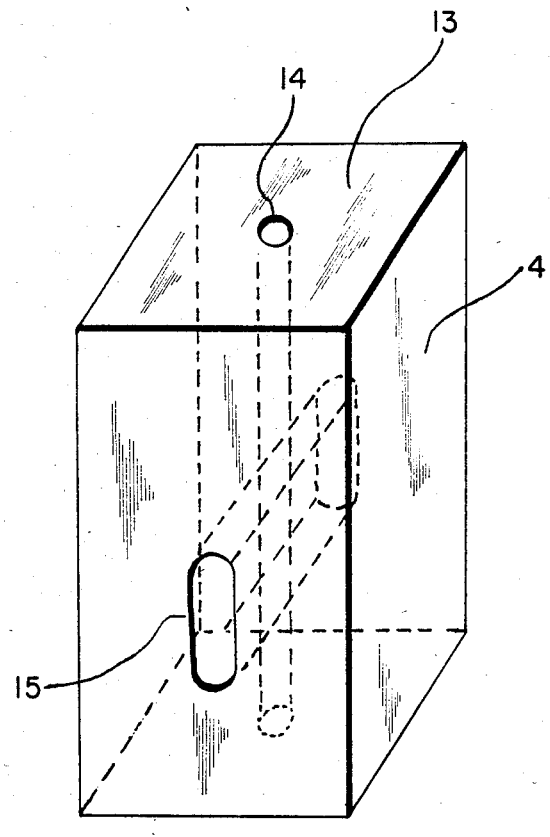
FIG. 2 is a perspective view of the sample holding cell of that nephelometer.

By referring to the figures, a laser nephelometer is disclosed which comprises a laser source (1) connected to a generator, whence comes an incident laser beam (2), of which the diameter equals that of the capillary tube (3), which is placed in the sample holder (4) that is detailed in FIG. 2. The incident ray (2) enters the capillary tube (3) fairly close to the separating zone (5) of the compounds to be studied. The scattered light (6) then crosses a diaphragm (7), and is received by a photosensing device that is connected to a photomultiplying device (8). The information received by device (8) is transmitted to a memory (9) which places it, either on a digital screen (10), or on a recording device (11), or on a printer (12).

The sample holding cell (4) is basically comprised (see FIG. 2) of a black metal or plastic block (13) which is pierced by a lengthwise orifice (14), designed to accomodate the capillary tube (3), and pierced in a crosswise and orthogonal direction to form a window (15) for the passing of luminous ray. In order to obtain a good reproduction of the measurements, it is important for the parts (3) and (4) to be perfectly adjusted and positioned.

EXAMPLE 1

The instruments used basically include:

a generator (1) which is the source of the laser beam (2) (helium-neon) and which is stablized (a variation of less than 5%);

a darkroom, as hermetic as possible, inside which there is the capillary tube (3) positioned in a sample holder (4); a photoelectronic sensor (8) such as a photoelectric cell which gathers scattered light connected to a photomultiplier;

an electronic memory (9);

a tracing or printing table (12) or a digital type display screen (10) designed to read the results.

In this example, the presence of a pneumococcus antigen in an adult cephalo-rachidian liquid is sensed.

Different samples of that selection are placed in various capillary tubes having an inner diameter of 0.8 mm, inside which ten microliters of that cephalo-rachidian liquid are sucked up, followed by five microliters of pneumococcic group antiserum.

The tip of the tubes is the sealed with wax. The tubes are then placed in the sample holder (4) of the laser nephelometer and the sample holder is placed inside the reading darkroom.

The device is switched on and the laser beam (2) which has a diameter of one millimeter, as a result of the assembly, falls right on the interface (5) between the antigen solution and the antibody solution.

On the numeric reader (10) or on the recording table (12), variations are observed. This demonstrates that the interface (5), is in fact in the precipitation zone.

The change of the curve is then observed which is:

flat when the reaction is negative, ascending when the reaction is positive and specific.

Hence, the specific antigen-antibody coupling, or the presence of a specific antigen can be detected.

The height and slope of the curve provide an evaluation of the amount of antigens which allows for an initial dosing.

EXAMPLE 2

This example pertains to the search for an antistaphylococcic antibody with staphygen (an antigen extracted from the golden staphylococcus).

After a two or three minute period of latency, if the serum contains the corresponding antibody, the intensity of scattered light rises by several steps.

The first extremely rapid increase is followed by a threshold of several minutes. A second slower rise, which is more significant occurs and then the phenomenon slows down in relation to time. After about fifteen minutes, it can be determined whether the reaction took place or not, whereas at that point, no precipitate is yet visible to the naked eye.

After several hours, the intensity of scattered light decreases. The volume of particles increases and a cloud appears, then flocculates can be observed.

When the serum is decomplemented through heating at 56 degrees C., only the first step can be observed.

Thus, this method is very useful in a hospital environment for dosing antigens in human serum. Indeed, sensing antigens that are present before the visible symptoms of the illness manifest themselves, makes a quick diagnosis possible, hence more effective in treatment. Heretofore, this type of sensing required a large amount of serum or of cephalo-rachidian liquid and a span of several hours, if not twenty-four.

Substituting the familiar vat with a capillary tube was never obvious. Indeed:

first, the capillary tube was known for a long time, well before nephelometry;

second, especially in a vat, the reaction is conducted in the entire volume of the vat, which makes it possible only to detect the beginning and the end of the reaction; however, in a capillary tube, since the section is thin, the evolution of the reaction can be observed;

third, the impact of walls facilitates precipitation and increases reaction kinetics, which decreases measuring time in unexpected proportions (twenty to thirty minutes as opposed to several hours);

finally, the capillary tube must display accurate characteristics, or an inner diameter which is close to that of the laser beam.

The device according to the invention displays many advantages. For example:

the measuring speed (of about twenty to thirty minutes instead of several hours with conventional methods);

the use of extremely small amounts of liquid (micromethod), which is more and more in demand and even required in a medical environment;

the possibility of observing the phenomenon before its emergence to the naked eye and even during its unfolding;

the possibility of analyzing the curve and to obtain a dosing of sensed antigens or antibodies;

the possibility of sensing antigens even in patients taking antibiotics;

the possibility of automating measurements;

the possibility of working with any laser beam source;

the possibility of achieving measurements which can be reproduced;

the possibility of throwing away the capillary tubes.

In this way, the device can be used successfully for any antigen or antibody search in clear or clarified liquids. For example:

antibiotic doses;

highlighting antigens or antibodies;

searching for circulating antigens.

The device can be used basically in a medical environment, but also can be used to sense food contamination.

We claim:

1. A laser nephelometer for detecting antigens and antibodies, comprising:

a laser source for emitting a laser beam;

a cell consisting of a capiliary tube containing a solution of said antigens and a solution of said antibodies to be detected, said laser beam being directed toward said cell and being scattered by said cell;

a photoelectric sensor to collect the scattered light of said laser beam;

processing means to process the information received by the sensor;

wherein the inner diameter of the capiliary tube is approximately equal to the diameter of the laser beam, and wherein the laser beam is directed perpendicular to the capiliary tube and falls in the vicinity of an interface separation zone between the antigen solution and antibody solution to be detected.

2. A nephelometer as recited in claim 1, wherein the capiliary tube is a cylindrical straight tube with an inner diameter of approximately one millimeter.

* * * * *